United States Patent
Wang et al.

(10) Patent No.: US 10,197,510 B2
(45) Date of Patent: Feb. 5, 2019

(54) VEHICLE TRACTION SYSTEM AND RADIATION IMAGING CHECK SYSTEM

(71) Applicant: Nuctech Company Limited, Beijing (CN)

(72) Inventors: Qiangqiang Wang, Beijing (CN); Quanwei Song, Beijing (CN); Hongqi Li, Beijing (CN); Yuan He, Beijing (CN); Junping Shi, Beijing (CN); Yucheng Dong, Beijing (CN); Huaping Li, Beijing (CN); Chao Guo, Beijing (CN)

(73) Assignee: Nuctech Company Limited, Beijing (CN)

( * ) Notice: Subject to any disclaimer, the term of this patent is extended or adjusted under 35 U.S.C. 154(b) by 48 days.

(21) Appl. No.: 15/280,765

(22) Filed: Sep. 29, 2016

(65) Prior Publication Data
US 2017/0184512 A1    Jun. 29, 2017

(30) Foreign Application Priority Data
Dec. 28, 2015 (CN) .......................... 2015 1 1001005

(51) Int. Cl.
*G01N 23/04*     (2018.01)
*G01V 5/00*     (2006.01)
*B66F 3/36*     (2006.01)

(52) U.S. Cl.
CPC ............... *G01N 23/04* (2013.01); *B66F 3/36* (2013.01); *G01V 5/0008* (2013.01); *B66F 2700/05* (2013.01); *G01N 2223/309* (2013.01)

(58) Field of Classification Search
CPC .................................................. G01N 23/04
See application file for complete search history.

(56) References Cited

U.S. PATENT DOCUMENTS

| 5,184,930 A | * | 2/1993 | Kuhn | ......................... B66F 5/04 |
| | | | | 187/208 |
| 5,484,134 A | * | 1/1996 | Francis | ..................... B66F 7/04 |
| | | | | 254/2 B |

(Continued)

FOREIGN PATENT DOCUMENTS

| CN | 101209705 A | 7/2008 |
| CN | 101434274 A | 5/2009 |

(Continued)

OTHER PUBLICATIONS

Machine Translation for CN 102 107 767 B (Nuctech Co Ltd) (2015).*

(Continued)

*Primary Examiner* — Edwin C Gunberg
(74) *Attorney, Agent, or Firm* — Knobbe Martens Olson & Bear LLP

(57) ABSTRACT

The present disclosure relates to vehicle traction apparatus and radiation imaging check systems. One illustrative implementation may comprise two parallel tracks, two sets of traction mechanisms and a driving unit, wherein the tracks are disposed on a ground. The two sets of traction mechanisms may be respectively disposed on the two tracks. Further, the driving unit may be adapted for driving the two sets of traction mechanisms to synchronously move along the two tracks. In some embodiments, each of the two sets of traction mechanisms includes a body, a cantilever, a lifting driving mechanism and a wheel supporting assembly, and may include features such as the body being mounted on the track, the cantilever being disposed parallel to a direction of the tracks, and/or both ends of the cantilever being respectively connected with the lifting driving mechanism and the wheel supporting assembly.

20 Claims, 5 Drawing Sheets

(56) References Cited

U.S. PATENT DOCUMENTS

| | | | |
|---|---|---|---|
| 5,704,295 A | 1/1998 | Lohr | |
| 5,911,408 A * | 6/1999 | Berends | B66F 7/04 |
| | | | 254/2 B |
| 6,966,540 B2 * | 11/2005 | Falk | B66F 5/04 |
| | | | 254/122 |
| 2008/0159840 A1 | 7/2008 | Hu et al. | |

FOREIGN PATENT DOCUMENTS

| | | |
|---|---|---|
| CN | 102107767 A | 6/2011 |
| CN | 102530791 A | 7/2012 |
| CN | 102107767 B | 2/2015 |
| CN | 104730591 A | 6/2015 |
| CN | 104742671 A | 7/2015 |
| CN | 205387339 | 7/2016 |
| GB | 245978 A | 5/2009 |
| JP | H08-99510 A | 4/1996 |

OTHER PUBLICATIONS

European Search Report dated May 8, 2017 received in EP Application No. 16189595.8 (6 pages).

Office Action dated May 26, 2017 in Chinese Application No. 201511001005.7 (8 pages); concise English-language summary thereof (2 pages); 1o pages total.

\* cited by examiner

US 10,197,510 B2

VEHICLE TRACTION SYSTEM AND RADIATION IMAGING CHECK SYSTEM

CROSS REFERENCE TO RELATED APPLICATION(S)

This application is based upon and claims benefit/priority of Chinese Patent Application No. 201511001005.7, filed on Dec. 28, 2015, published as CN105621039 A, which are incorporated herein by reference in entirety.

BACKGROUND

Technical Field

The present disclosure generally relates to the technical field of manufacture of the radiation imaging checking equipments, and specifically relates to the vehicle traction apparatus and a radiation imaging checking system.

Description of Related Information

A radiation imaging checking system is necessary for detection equipments of the customs, airports and railways. The checking equipments include a detection channel, and a radiation source and an array detector mounted within the detection channel. When a vehicle to be detected(for example, a vehicle loaded with containers) passes through the detection channel and passes the radiation source, a ray beam emitted by the radiation source penetrates through the vehicle to be detected, and is received by the array detector. The array detector is adapted for converting an intensity of the ray beam to gray-scale of an image, thereby obtaining a transmission image of objects loaded in the vehicle to be detected.

At present, generally by use of a vehicle traction apparatus, front wheels of the vehicle to be detected are fixed, and the vehicle to be detected is dragged to move and pass through the detection channel. Conventional vehicle traction apparatus can be divided into two types, and one type of the vehicle traction apparatus disposes tracks and a traction wagon under the ground, to avoid the traction wagon from shadowing the vehicle to be detected and thus affecting a detection result. However, installation of this type of the vehicle traction apparatus relates to civil construction and equipments installation, wherein the civil construction has a large scale, resulting in high production and usage cost and inconvenient maintenance.

Other type of the vehicle traction apparatus has a structure as shown in FIG. 1, and includes two parallel tracks (not shown in FIG. 1), two front fork arms 1, two rear fork arms (not shown in FIG. 1), lifting mechanism 3 and rotary driving mechanism (not shown in FIG. 1). The tracks are disposed on a ground; the two front fork arms 1 are respectively disposed on an inner side of the two tracks; and the two rear fork arms are respectively disposed on an inner side of the two tracks, and spaced apart from a respective front rear fork arm in a direction parallel to the tracks. The number of the rotary driving mechanism is four, and each of the rotary driving mechanism is used for driving a corresponding one of the two front fork arms 1 and two rear fork arms to rotate around a rotary shaft 4, to a position (a position as shown in FIG. 1) where the corresponding one of the two front fork arms 1 and two rear fork arms is perpendicular to the track for fixing the front wheels of the vehicle to be detected, or to a position where the corresponding one of the two front fork arms 1 and two rear fork arms is parallel to the track in order for the vehicle to be detected to pass. The number of the lifting mechanisms 3 is four, and each of the lifting mechanism 3 is disposed on an outer side of a corresponding one of the two front fork arms 1 and the two rear fork arms, for driving the two front fork arms 1 and the two rear fork arms to move up or down synchronously.

This type of the vehicle traction apparatus is disposed on the ground, and thus the civil works and production and usage cost can be reduced. However, there is an inevitable problem during usage:

In this vehicle traction apparatus, four lifting mechanisms individually drives the two front fork arms and the two rear fork arms to move up and down, the footprint is large and the cost is high. Moreover, since each of the lifting mechanism 3 is disposed on the outer side of a corresponding one of the two front fork arms 1 and the two rear fork arms, the lifting mechanism 2 with a higher height will shadow a bottom of the vehicle to be detected when it is prospectively imaged, and the shadowed area is large. Thus, the imaging effect and imaging scope of the vehicle to be detected will be affected adversely.

OVERVIEW OF SOME ASPECTS

The present disclosure is to at least resolve one of the technical problems existing in the prior art, and provides a vehicle traction apparatus and a radiation imaging check system, which has a simple civil works, a small footprint and a low cost, and also a shadowed area of the vehicle to be detected is smaller, and thus the imaging effect and the imaging scope of the vehicle to be detected will not be affected adversely.

One aspect of the present disclosure provides a vehicle traction apparatus, comprising two parallel tracks, two sets of traction mechanisms and a driving unit, wherein the tracks are disposed on a ground; the two sets of traction mechanisms are respectively disposed on the two tracks; the driving unit is adapted for driving the two sets of traction mechanisms to synchronously move along the two tracks; characterized in that, each of the two sets of traction mechanisms includes a body, a cantilever, a lifting driving mechanism and a wheel supporting assembly, wherein the body is mounted on the track; the cantilever is disposed parallel to a direction of the tracks, and both ends of the cantilever are respectively connected with the lifting driving mechanism and the wheel supporting assembly; the wheel supporting assembly is adapted for fixing front wheels of a vehicle to be detected; the lifting driving mechanism is disposed on the body, for driving the wheel supporting assembly to move up and down.

According to some implementations, the vehicle traction apparatus comprises a portal frame, two ends of which are respectively connected with the bodies of the two sets of traction mechanisms, the portal frame is adapted for ensuring balance of forces applied on the wheel supporting assembly when it fixing the front wheels of the vehicle to be detected.

In some embodiments, the vehicle traction apparatus comprises two balance tracks, each of which is disposed on an outer side of a corresponding one of the two tracks and parallels to the tracks, the two balance tracks are adapted for ensuring balance of forces applied on the wheel supporting assembly when it fixing the front wheels of the vehicle to be detected.

Further, the wheel supporting assembly may comprise two front fork arms, two rear fork arms, and four rotary driving mechanisms, wherein the two front fork arms are respectively disposed on an inner side of the two tracks oppositely, and each of the two front fork arms is connected with a corresponding cantilever and is rotatable relative to corresponding cantilever in a horizontal plane; the two rear fork arms are respectively disposed on an inner side of the two tracks oppositely, and respectively spaced apart from the two front fork arms in the direction parallel to the tracks, each of the rear fork arms is connected with a corresponding cantilever and is rotatable relative to the corresponding cantilever in a horizontal plane; each of the four rotary driving mechanisms are adapted for driving a corresponding one of the two front fork arms and the two rear fork arms, to rotate to a position where the corresponding one of the two front fork arms and the two rear fork arms is parallel to the tracks or a position where the corresponding one of the two front fork arms and the two rear fork arms is perpendicular to the tracks.

According to aspects herein, the rotary driving mechanism includes a rotary shaft and a boom cylinder, wherein the rotary shaft is disposed perpendicular to the ground and rotatably connected with the cantilever; each of the two front fork arms and the two rear arms is fixedly connected with a corresponding one of the four rotary driving mechanisms; the boom cylinder is adapted for providing rotary power to the rotary shaft.

In some aspects, the body includes a main body and an extended arm, wherein the main body is provided with a plurality of wheels, which is capable of rolling along the tracks; one end of the extended arm is connected with the main body, and the extended arm extends from the end to the other end at an outer side of the cantilever, and a height of the extended arm is lower than that of the cantilever.

Further, the vehicle traction apparatus may further include a control unit, and the control unit is adapted for controlling operation of the driving unit, each of the lifting driving mechanisms and each of the rotary driving mechanisms.

Consistent with some implementations, the lifting driving mechanism may include a guiding shaft and a lifting oil cylinder, wherein the guiding shaft is disposed perpendicular to the ground, and is fixed on the body; the lifting oil cylinder is disposed on the body and the wheel supporting assembly, for driving the wheel supporting assembly to move up or down along the guiding shaft.

As another technical solution, the present disclosure provides a radiation imaging check system, comprising a detection channel, a vehicle traction apparatus, a radiation source and an array detector, wherein, the vehicle traction apparatus is adapted for dragging a vehicle to be detected to pass through the detection channel; the radiation source and the array detector are oppositely disposed on two sides of an inner side of the detection channel, a ray beam emitted from the radiation source penetrates through the vehicle to be detected, and is received by the array detector; the vehicle traction apparatus is the vehicle traction apparatus according to various innovations and implementations herein.

Some features, aspects and/or advantages of the present disclosure are set forth as below.

The vehicle traction apparatus provided by the present disclosure is capable of driving a single wheel supporting assembly (including multiple components like the front fork arm and the rear fork arm) to move up and down integrally by a single lifting driving mechanism, by means of connecting the lifting driving mechanism and the wheel supporting assembly together via a cantilever. Thus, the vehicle traction apparatus of the present disclosure can reduce a number of the lifting driving mechanisms, thus reducing the footprint and lowering the production and usage cost. Moreover, there is a certain distance from the lifting driving mechanism and the wheel supporting assembly in the direction parallel to the track due to a presence of the cantilever. This lowers a height of the vehicle traction apparatus at the wheel supporting assembly, which corresponds to a height of the wheel supporting assembly per se (only about 400 mm). Thus, a shadowed area of the vehicle to be detected can be reduced, and imaging effect and imaging scope of the vehicle to be detected will not be affected adversely.

The radiation imaging check system provided by the present disclosure has a simple civil works, a small footprint and a low cost, by use of vehicle traction apparatus of the present disclosure. Also, a shadowed area of the vehicle to be detected is smaller, and thus the imaging effect and the imaging scope of the vehicle to be detected will not be affected adversely.

DETAILED DESCRIPTION OF ILLUSTRATIVE IMPLEMENTATIONS

Figure 1:
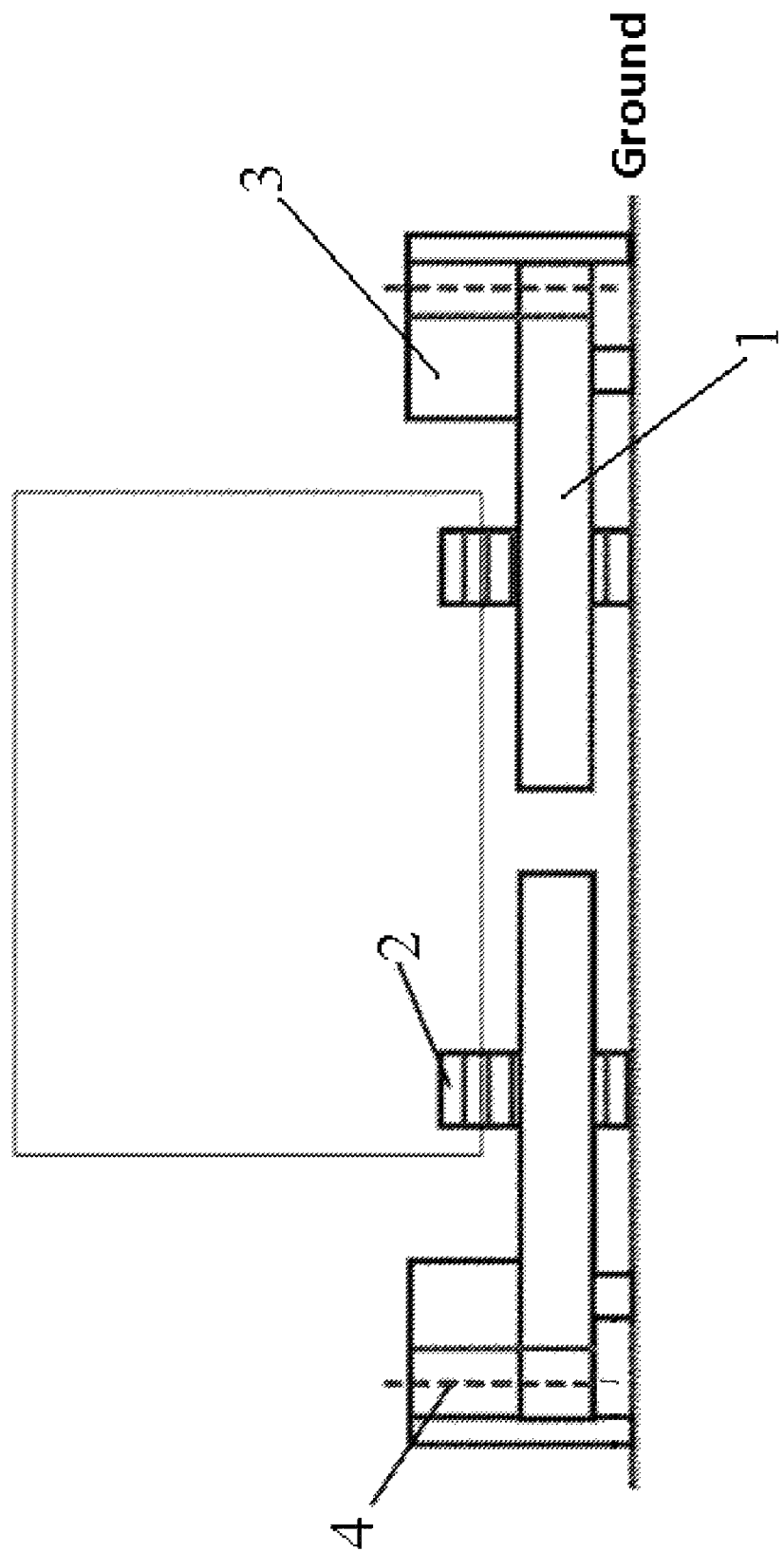
FIG. 1 is a structural diagram of a vehicle traction apparatus of prior art.

In order for those skilled in the art understanding the technical solutions of the present disclosure better, in the following, a vehicle traction apparatus and a radiation imaging check system provided by the present disclosure will be described in detail by referring the accompany drawings.

Referring to FIGS. 2-5, a vehicle traction apparatus provided by the present disclosure provided by the present disclosure includes two parallel tracks 10, two sets of traction mechanisms and a driving unit (not shown in the drawings). Wherein the two tracks 10 are provided on the ground, and the two sets of traction mechanisms are set on the two tracks 10 respectively, for fixing and uplifting a vehicle to be detected. The driving unit is adapted for driving the two sets of the traction mechanisms to move simultaneously along the two tracks 10, thereby driving the vehicle to be detected to move.

In the present example, each set of the traction mechanism includes a body 11, a cantilever 12, a lifting driving mechanism 13 and a wheel supporting assembly. Wherein, the body 11 is mounted on the track 10; and the cantilever 12 is disposed in an extending direction of the track 10 and on an inner side of the body 11 and two ends of the cantilever 12 are respectively connected to the lifting driving mechanism 13 and the wheel supporting assembly. The wheel supporting assembly is used for fixing front wheels of the vehicle to be detected, and includes two front fork arms 14, two rear fork arms 15 and four rotary driving mechanisms. The two front fork arms 14 are respectively disposed on an inner side of the tracks 10 oppositely, and each front arm 14 is connected to a corresponding cantilever 12 and can rotate in a horizontal plane. The two rear fork arms 15 are respectively disposed on an inner side of the tracks 10 oppositely and respectively spaced apart from the front arm 14 in a direction parallel to the tracks 10. That is to say, the two rear fork arms 15 are disposed oppositely to each other and are respectively located at a rear side of the front fork arms 14.

Each of the rear fork arms 15 is also connected to a corresponding cantilever 12 and can rotate in the horizontal plane.

Figure 3:
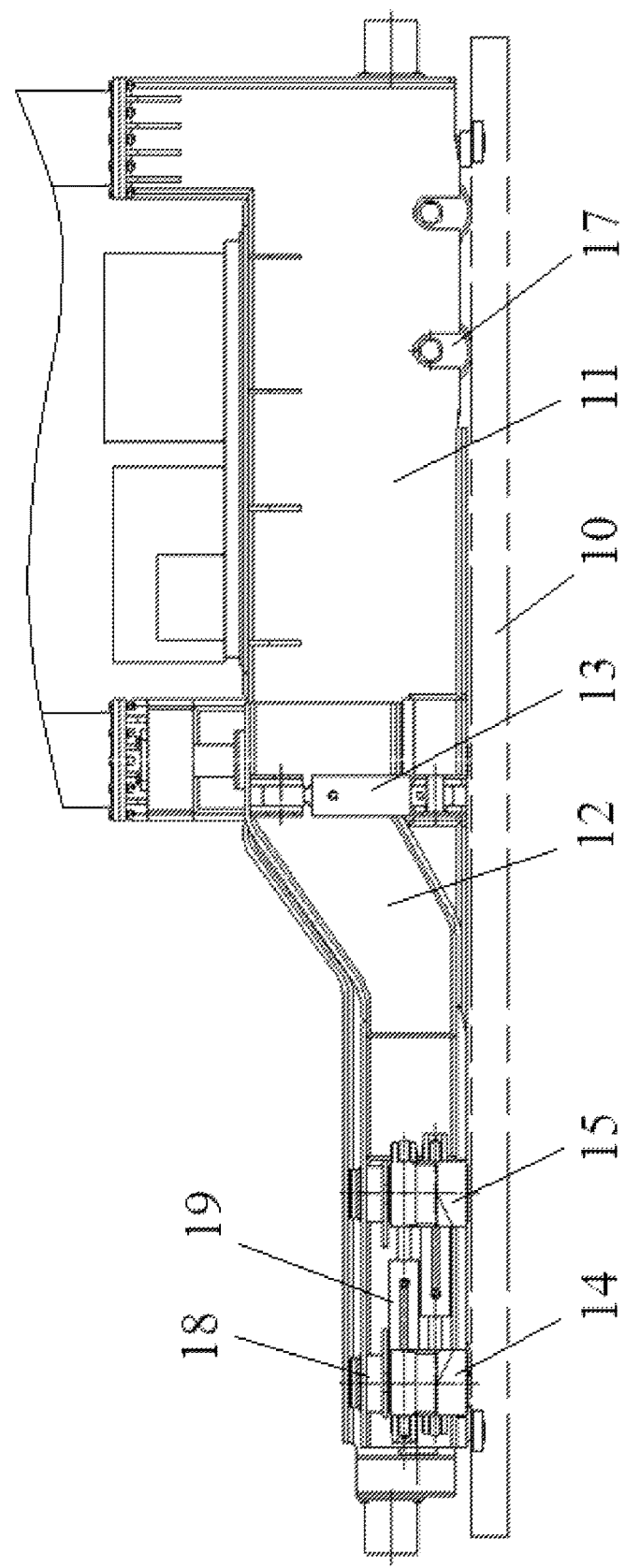
FIG. 3 is a partial side view of the vehicle traction apparatus as shown in FIG. 2.
Figure 4:
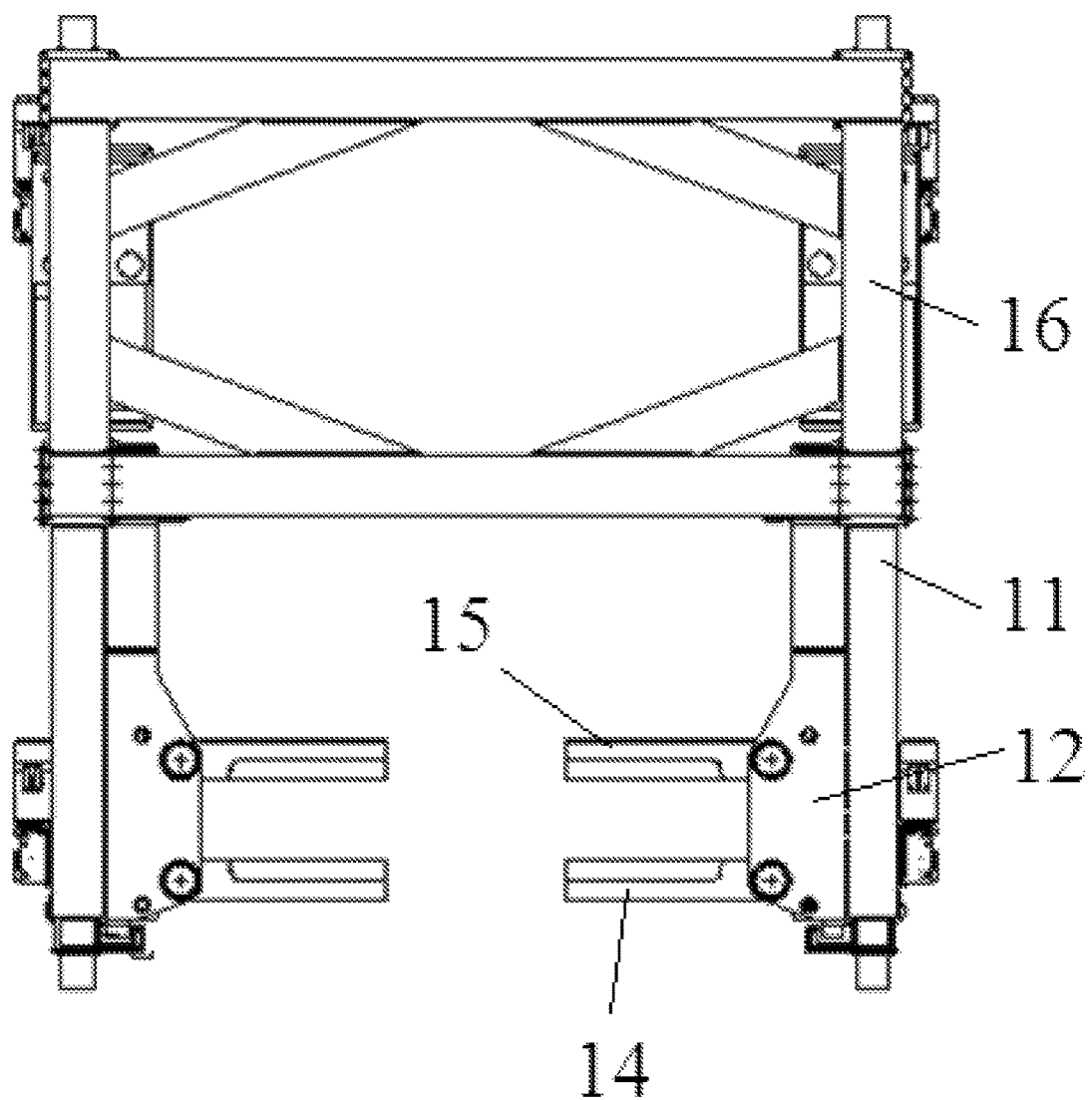
FIG. 4 is a top view of the vehicle traction apparatus as shown in FIG. 2.

Each of the four rotary driving mechanisms is used for driving a corresponding one of the two front fork arms 14 and the two rear fork arms 15 to rotate to a position where the corresponding one of the two front fork arms 14 and the two rear fork arms 15 is parallel to the tracks 10 or a position where the corresponding one of the two front fork arms 14 and the two rear fork arms 15 is perpendicular to the tracks 10. FIG. 4 shows that the two front fork arms 14 and the two rear fork arms 15 are all located in the position where they are perpendicular to the tracks 10. Each rotary driving mechanism includes a rotary shaft 18 and a boom cylinder 19. As shown in FIG. 3, the rotary shaft 18 is disposed vertically relative to the ground, and is rotatably connected with the cantilever 12. Each one of the two front fork arms 14 and two rear fork arms 15 is fixedly connected with the rotary shaft 18 of a corresponding one of the four rotary driving mechanisms. The boom cylinder 19 is used for providing rotary power to the rotary shaft 18, so that a corresponding one of the front fork arms 14 and the rear fork arms 15 can be driven by the rotary shaft 18 to rotate around it, to the position where the corresponding one of the front fork arms 14 and the rear fork arms 15 is parallel to the tracks 10 or to the position the corresponding one of the front fork arms 14 and the rear fork arms 15 is perpendicular to the tracks 10. Of course, any other structures can be adopted for the rotary driving mechanism, as long as the front fork arms or the rear fork arms can be driven to rotate. The present disclosure is not intended to limit the specific structure of the rotary driving mechanism. Further, the rotary driving mechanism can be integrally fixed on the cantilever 12, to move up or down synchronously together with the cantilever 12. Alternatively, a portion (for example, the cylinder) of the rotary driving mechanism can be fixed on the body 11 while a portion for driving can be fixed on the cantilever 12, but the rotary driving mechanism shall be able to drive the front fork arms or the rear fork arms to rotate without interfering with the cantilever 12 to move up and down.

The lifting driving mechanism 13 is disposed on the body 11, for driving the wheel supporting assembly to move up or down, that is, for driving the front fork arm 14 and the rear fork arm 14 on a same track 10 to move up or down at the same time, so that a single lifting driving mechanism 13 is capable of driving a single wheel supporting assembly integrally. The lifting driving mechanism 13 specifically includes a guiding shaft and a lifting oil cylinder. The guiding shaft is disposed perpendicular to the ground, and is fixed on the body 11. A stationary end of the lifting oil cylinder is disposed on the body 11, and a movable end of the lifting oil cylinder is disposed on the wheel supporting assembly for driving the wheel supporting assembly to move up or down along the guiding shaft.

It is capable of driving a single wheel supporting assembly (including the components like the front fork arm 14 and the rear fork arm 15 on the same track 10) to move up and down integrally for a single lifting driving mechanism 13, by means of connecting the lifting driving mechanism 13 and the wheel supporting assembly together via the cantilever 12. Comparing with the prior art, the vehicle traction apparatus of the present disclosure can reduce a number of the lifting driving mechanisms 13, thus reducing the footprint and lowering the production and usage cost. Moreover, there is a certain distance from the lifting driving mechanism 13 and the wheel supporting assembly in the direction parallel to the track 10 due to a presence of the cantilever 12. This lowers a height of the vehicle traction apparatus at the wheel supporting assembly, which corresponds to a height of the wheel supporting assembly per se (only about 400 mm). Thus, a shadowed area of the vehicle to be detected can be reduced, and imaging effect and imaging scope of the vehicle to be detected will not be affected adversely. As shown in FIG. 3, since both heights of the body 11 and the lifting driving mechanism 13 are higher than that of the wheel supporting assembly, a right end of the cantilever 12 connected between the lifting driving mechanism 13 and the wheel supporting assembly is higher than a left end thereof, that is, the cantilever 12 has a bent portion inclined downwardly.

Figure 2:
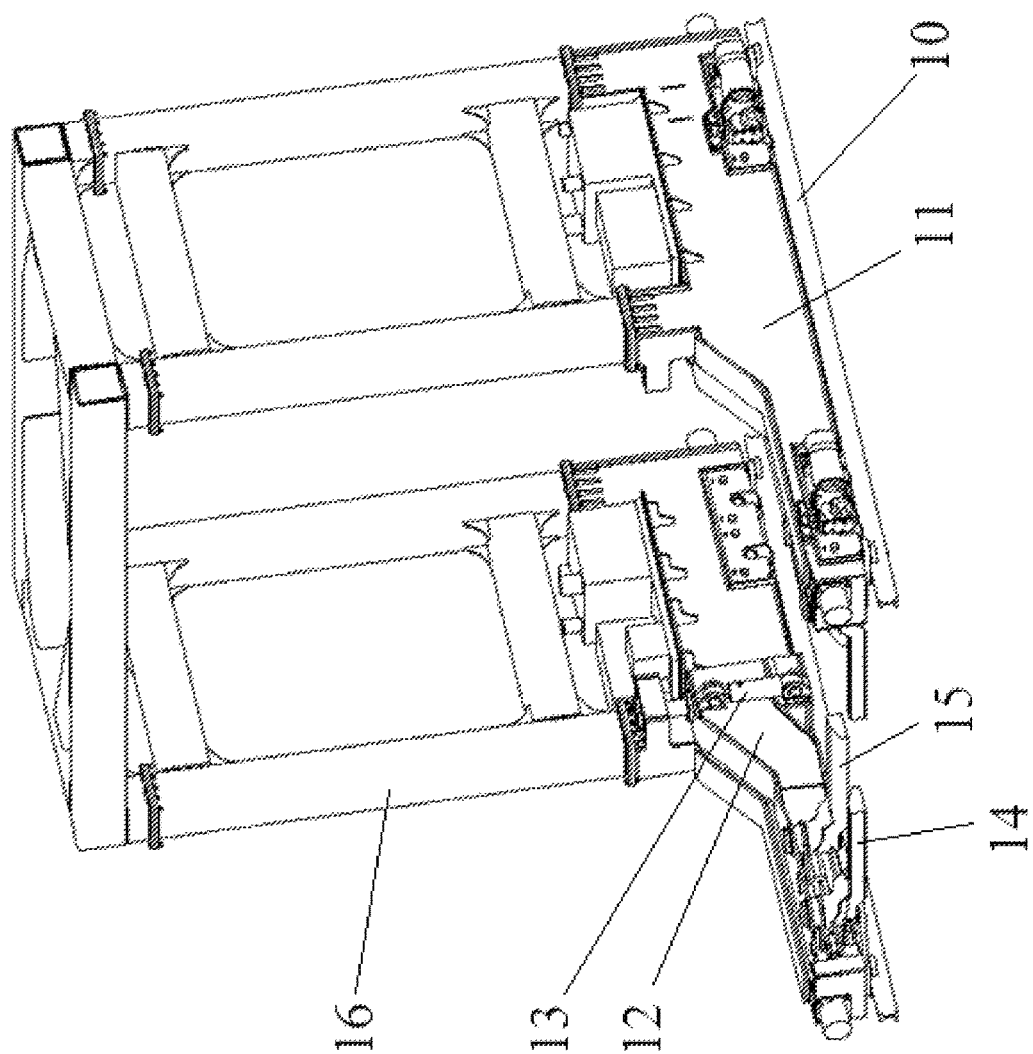
FIG. 2 is a perspective view of a vehicle traction apparatus according to an example of the present disclosure.

According to some implementations, the vehicle traction apparatus further includes a portal frame 16. Both ends of the portal frame 16 are respectively connected to the bodies 11 of the two sets of the traction mechanisms, to ensure balance of forces applied on the wheel supporting assembles when it fixed the front or rear wheels of the vehicle to be detected. The advantages of the portal frame 16 lies in that: the portal frame 16 can improve the stability of the vehicle to be detected when moving along the tracks 10 and structural stability and safety of the vehicle traction apparatus; also, the portal frame 16 can be disassembled conveniently, and structure and weight of the portal frame 16 can be adjusted according to a load type and other specific conditions of the vehicle to be detected in practical applications, so that the vehicle traction apparatus can be applied to a various different types of vehicles and thus have a larger range of applications. Further, the portal frame 16 is constituted by two connecting columns and a beam. As shown in FIG. 2, the two connecting columns are disposed perpendicular to the ground, and are respectively connected to the two bodies 11. The beam is disposed horizontally, with both ends respectively connected with the two connecting columns. A gravity of the portal frame 16 is constituted by a gravity of the two connecting columns and a gravity of the beam. That is to say, a pressure applied to the vehicle traction apparatus by the portal frame 16 is equivalent to a sum of the gravities of the two connecting columns and the beam. The sum of the gravities shall be larger than a pressure applied to the wheel supporting assembly by the vehicle to be detected, to ensure balance of forces applied on the wheel supporting assembly.

Of course, in practice, the above-described portal frame 16 can be replaced with two balance tracks, or both the two balance tracks and portal frame can be used. Specifically, the two balance tracks are parallel to each other, and each one can be disposed on one side (an outer side) of a respective track in parallel. The balance tracks function the same as the portal frame 16, to ensure the balance of forces applied on the wheel supporting assembly when the wheel supporting assembly fixing the front wheels of the vehicle to be detected, improving the stability of the whole vehicle traction apparatus.

Further, to improve the structural stability, the body 11 may further include a main body and an extended arm. The main body is provided with a plurality of wheels 17, which can be driven by the driving unit to roll along the track 10, so that the traction apparatus can move as a whole. One end (a right end as shown in FIG. 3) of the extended arm is connected with the main body, and the extended arm extends from the one end to the other end (a left end as shown in FIG. 3) at an outer side of the cantilever 12. Moreover, the extended arm has a similar shape and size as the cantilever, and a height of the extended arm is smaller than that of the cantilever 12, so that the height of the vehicle traction apparatus at the wheel supporting assembly, which corresponds to the height of the wheel supporting assembly per se, remains unchanged (the same as that of the cantilever). Of course, in practice, the extended arm can be formed in other shapes, as long as the height of the extended arm is lower than that of the cantilever. Further, the structure of the body 11 is not limited to that adopted in the present example, and any other structure can be used in practice.

Figure 5:
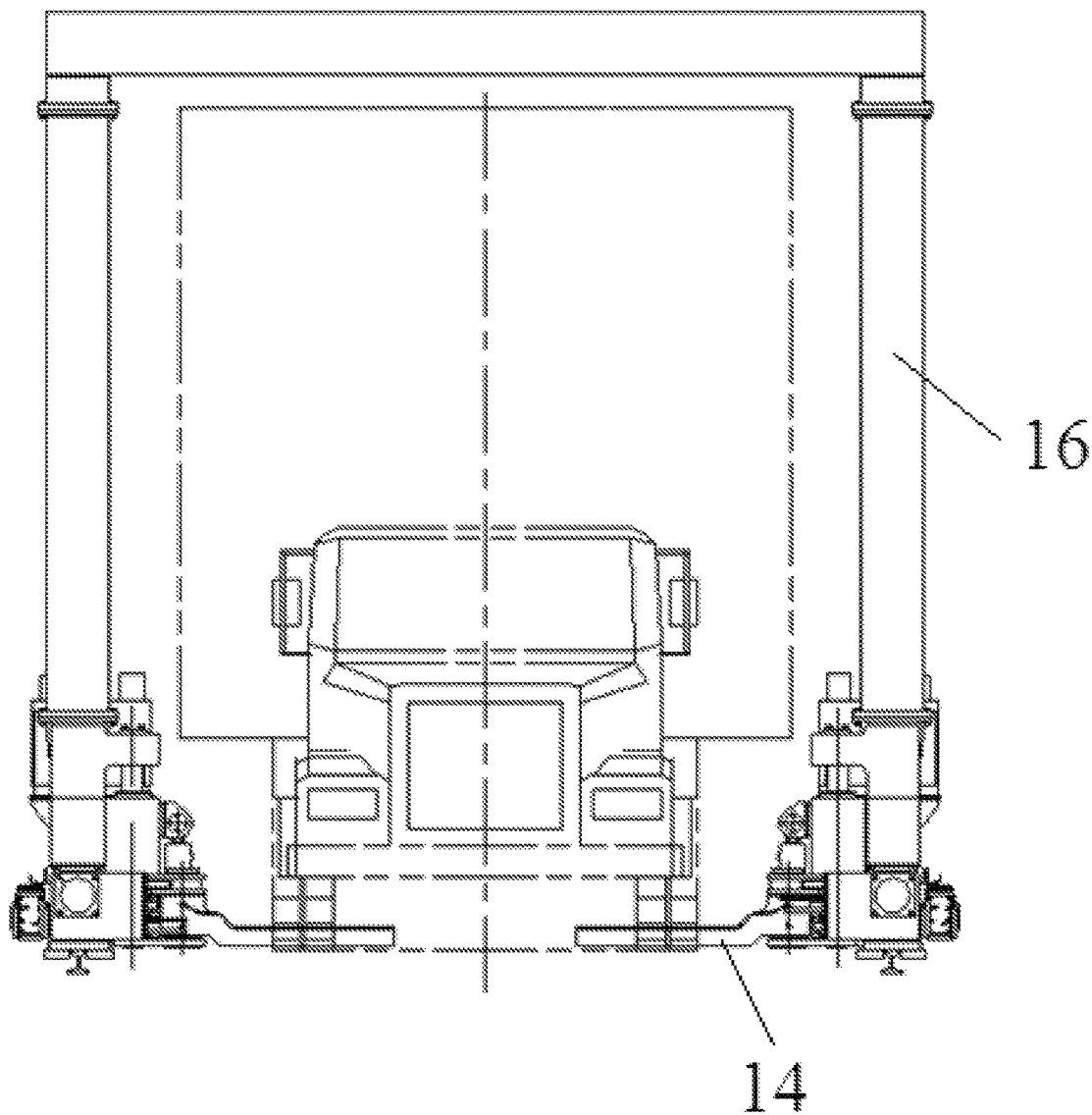
FIG. 5 is a front view of the vehicle traction apparatus as shown in FIG. 2.

When checking the vehicle to be detected by radiation imaging, at first, the two front fork arms 14 are driven by their respective rotary driving mechanisms to rotate to the position where they are perpendicular to the track 10, and at this moment, the two rear fork arms 15 are still located at the position where they are parallel to the track 10. Then, the vehicle to be detected is moved forward until that the front wheels contact with the two front fork arms 14, as shown in FIG. 5. The two rear fork arms 15 are driven by their respective rotary driving mechanisms to rotate to the position where they are perpendicular to the track 10. At this moment, each of the rear fork arm 15 and the front fork arm 14 at the same track parallels to each other and can clamp the front wheel of the vehicle to be detected together, so that the front wheels of the detected wheels can be fixed. Then, both of the lifting driving mechanisms 13 on the respective track drives two integral wheel supporting assembly to move up synchronously, so that the front wheels of the vehicle to be detected can be lifted.

According to some aspects, the vehicle traction apparatus may further include a control unit. The control unit is used for controlling operation of the driving unit, each lifting driving mechanism and each rotary driving mechanism, to automatically control the movement of the traction mechanism as a whole, the synchronously up and down movement of the two front fork arms 14 and the two rear fork arms 15 and their respective rotary movements.

It shall be understood that, consistent with one or more of the present examples, the wheel supporting assembly includes a pair of front fork arms 14 and a pair of rear fork arms 15, for fixing the front wheels of the vehicle to be detected. However, the present disclosure is not limited to this. In practice, the wheel supporting assembly also can include two pairs of the front fork arms and two pairs of the rear fork arms, for fixing the front wheels of the vehicle to be detected. Or, the wheel supporting assembly also can include three or more pairs of the front fork arms and three or more pairs of the rear fork arms, according to specific conditions, to satisfy different requirements of for example some special types of vehicles. A number of the rotary driving mechanisms can be adjusted adaptively according to a total number of the front fork arms and the rear fork arms.

As described above, the vehicle traction apparatus provided by the examples of the present disclosure, is capable of driving an integral wheel supporting assembly (including various components such as the front and rear fork arms) to move up and down by a single lifting driving mechanism, by means of connecting the lifting driving mechanism with the wheel supporting assembly by use of a cantilever, and thus can reduce a number of the lifting driving mechanisms, thereby reducing a footprint, and production and usage cost of the apparatus. Moreover, there is a certain distance from the lifting driving mechanism and the wheel supporting assembly in a direction parallel to a track due to a presence of the cantilever 12, and this lowers a height of the vehicle traction apparatus at the wheel supporting assembly, which corresponds to a height of the wheel supporting assembly per se. Thus, a shadowed area of the vehicle to be detected can be reduced, and imaging effect and imaging scope of the vehicle to be detected will not be affected adversely. Additionally, since the whole vehicle traction apparatus is installed on the ground, no complex civil work is needed, and thus the production and usage cost of the apparatus can be reduced.

As another technical solution, implementations of the present disclosure may provide a radiation imaging check system, which includes a detection channel, a vehicle traction apparatus, a radiation source and an array detector. The vehicle traction apparatus is adapted for driving a vehicle to be detected to passing through the detection channel, and it can be the vehicle traction apparatus provided by the above-described examples of the present disclosure. The radiation source and the array detector are mounted oppositely to each other on two opposite sides inside the detection channel. A ray beam emitted by the radiation source penetrates through the vehicle to be detected and received by the array detector. The array detector converts intensities of the received ray beam to gray-scales of image, and thus obtaining a transmission image of objects loaded within the vehicle to be detected.

The radiation imaging check system provided by the present disclosure has a simple civil works, a small footprint and a low cost, by use of the above-described vehicle traction apparatus provided by the present disclosure. Also, a shadowed area of the vehicle to be detected is smaller, and thus the imaging effect and the imaging scope of the vehicle to be detected will not be affected adversely.

It should be understood that, the above examples are merely exemplary implementations which are intended to illustrate the principle of the present disclosure, and the present disclosure are not limited to these examples. Those skilled in the art can make various modification and improvements without departing from the spirit and essence of the disclosure and innovations/inventions herein. These modifications and improvements are also regarded as falling within the protective scope of the present disclosure.

What is claimed is:

1. A vehicle traction apparatus, comprising:
   two parallel tracks,
   two sets of traction mechanisms, and
   a driving unit,
   wherein the tracks are disposed on a ground;
   wherein the two sets of traction mechanisms are respectively disposed on the two tracks;
   wherein the driving unit is adapted for driving the two sets of traction mechanisms to synchronously move along the two tracks;
   wherein each of the two sets of traction mechanisms includes a body, a cantilever, a lifting driving mechanism and a wheel supporting assembly,
   wherein the body is mounted on the track;
   wherein the cantilever is disposed parallel to a direction of the tracks, and both ends of the cantilever are respectively connected with the lifting driving mechanism and the wheel supporting assembly;
   wherein the wheel supporting assembly is adapted for fixing front wheels of a vehicle to be detected;
   wherein the lifting driving mechanism is disposed on the body, and is connected to the cantilever such that the lifting driving mechanism drives the cantilever to move up and down in entirety so as to carry the wheel supporting assembly to move up and down; and
   wherein the vehicle traction apparatus further comprises a portal frame, two ends of which are respectively connected with the bodies of the two sets of traction mechanisms opposite to the wheel supporting assemblies, so as to balance forces applied on the wheel supporting assemblies when they supporting the front wheels of the vehicle to be detected.

2. The vehicle traction apparatus according to claim 1, wherein the vehicle traction apparatus comprises two balance tracks, each of which is disposed on an outer side of a corresponding one of the two tracks and parallels to the tracks, wherein the two balance tracks are adapted for ensuring balance of forces applied on the wheel supporting assembly when it fixing the front wheels of the vehicle to be detected.

3. The vehicle traction apparatus according to claim 1, wherein the wheel supporting assembly comprises two front fork arms, two rear fork arms, and four rotary driving mechanisms, wherein:
the two front fork arms are respectively disposed on an inner side of the two tracks oppositely, and each of the two front fork arms is connected with a corresponding cantilever and is rotatable relative to corresponding cantilever in a horizontal plane;
the two rear fork arms are respectively disposed on an inner side of the two tracks oppositely, and respectively spaced apart from the two front fork arms in the direction parallel to the tracks, each of the rear fork arms is connected with a corresponding cantilever and is rotatable relative to the corresponding cantilever in a horizontal plane;
each of the four rotary driving mechanisms are adapted for driving a corresponding one of the two front fork arms and the two rear fork arms, to rotate to a position where the corresponding one of the two front fork arms and the two rear fork arms is parallel to the tracks or a position where the corresponding one of the two front fork arms and the two rear fork arms is perpendicular to the tracks.

4. The vehicle traction apparatus according to claim 3, wherein the rotary driving mechanism includes a rotary shaft and a boom cylinder, wherein:
the rotary shaft is disposed perpendicular to the ground and rotatably connected with the cantilever; each of the two front fork arms and the two rear arms is fixedly connected with a corresponding one of the four rotary driving mechanisms; and
the boom cylinder is adapted for providing rotary power to the rotary shaft.

5. The vehicle traction apparatus according to claim 4, wherein the body includes a main body and an extended arm, wherein:
the main body is provided with a plurality of wheels, which are capable of rolling along the tracks; and
one end of the extended arm is connected with the main body, and the other end of the extended arm extends from the one end to the other end at an outer side of the cantilever, wherein a height of the extended arm is lower than that of the cantilever.

6. The vehicle traction apparatus according to claim 4, wherein the vehicle traction apparatus further includes a control unit, wherein the control unit is adapted for controlling operation of the driving unit, each of the lifting driving mechanisms and each of the rotary driving mechanisms.

7. The vehicle traction apparatus according to claim 1, wherein the lifting driving mechanism includes a guiding shaft and a lifting oil cylinder, wherein:
the guiding shaft is disposed perpendicular to the ground, and is fixed on the body; and
the lifting oil cylinder is disposed on the body and the wheel supporting assembly, for driving the wheel supporting assembly to move up or down along the guiding shaft.

8. The vehicle traction apparatus according to claim 1, wherein the portal frame is configured to be disassembled.

9. The vehicle traction apparatus according to claim 1, wherein structure and weight of the portal frame is configured to be adjusted according to a load type of the vehicle.

10. The vehicle traction apparatus according to claim 1, wherein the portal frame comprises two connecting columns and a beam.

11. A radiation imaging check system, comprising a detection channel, a vehicle traction apparatus, a radiation source and an array detector, wherein, the vehicle traction apparatus is adapted for dragging a vehicle to be detected to pass through the detection channel;
wherein the radiation source and the array detector are oppositely disposed on two sides of an inner side of the detection channel, a ray beam emitted from the radiation source penetrates through the vehicle to be detected, and is received by the array detector;
wherein the vehicle traction apparatus comprising two parallel tracks, two sets of traction mechanisms and a driving unit, wherein the tracks are disposed on a ground; the two sets of traction mechanisms are respectively disposed on the two tracks; the driving unit is adapted for driving the two sets of traction mechanisms to synchronously move along the two tracks;
wherein each of the two sets of traction mechanisms includes a body, a cantilever, a lifting driving mechanism and a wheel supporting assembly, and wherein:
the body is mounted on the track;
the cantilever is disposed parallel to a direction of the tracks, and both ends of the cantilever are respectively connected with the lifting driving mechanism and the wheel supporting assembly;
the wheel supporting assembly is adapted for fixing front wheels of a vehicle to be detected;
the lifting driving mechanism is disposed on the body, and is connected to the cantilever such that the lifting driving mechanism drives the cantilever to move up and down in entirety so as to carry the wheel supporting assembly to move up and down; and
wherein the vehicle traction apparatus further comprises a portal frame, two ends of which are respectively connected with the bodies of the two sets of traction mechanisms opposite to the wheel supporting assemblies, so as to balance forces applied on the wheel supporting assemblies when they supporting the front wheels of the vehicle to be detected.

12. The radiation imaging check system according to claim 11, wherein the vehicle traction apparatus comprises two balance tracks, each of which is disposed on an outer side of a corresponding one of the two tracks and parallels to the tracks, wherein the two balance tracks are adapted for ensuring balance of forces applied on the wheel supporting assembly when it fixing the front wheels of the vehicle to be detected.

13. The radiation imaging check system according to claim 11, wherein the wheel supporting assembly comprises two front fork arms, two rear fork arms, and four rotary driving mechanisms, wherein:
the two front fork arms are respectively disposed on an inner side of the two tracks oppositely, and each of the two front fork arms is connected with a corresponding cantilever and is rotatable relative to corresponding cantilever in a horizontal plane;

the two rear fork arms are respectively disposed on an inner side of the two tracks oppositely, and respectively spaced apart from the two front fork arms in the direction parallel to the tracks, each of the rear fork arms is connected with a corresponding cantilever and is rotatable relative to the corresponding cantilever in a horizontal plane; and each of the four rotary driving mechanisms are adapted for driving a corresponding one of the two front fork arms and the two rear fork arms, to rotate to a position where the corresponding one of the two front fork arms and the two rear fork arms is parallel to the tracks or a position where the corresponding one of the two front fork arms and the two rear fork arms is perpendicular to the tracks.

14. The radiation imaging check system according to claim 13, wherein the rotary driving mechanism includes a rotary shaft and a boom cylinder, wherein:

the rotary shaft is disposed perpendicular to the ground and rotatably connected with the cantilever; each of the two front fork arms and the two rear arms is fixedly connected with a corresponding one of the four rotary driving mechanisms; and the boom cylinder is adapted for providing rotary power to the rotary shaft.

15. The radiation imaging check system according to claim 14, wherein the body includes a main body and an extended arm, wherein:

the main body is provided with a plurality of wheels, which are capable of rolling along the tracks; and one end of the extended arm is connected with the main body, and the other end of the extended arm extends from the one end to the other end at an outer side of the cantilever, wherein a height of the extended arm is lower than that of the cantilever.

16. The radiation imaging check system according to claim 14, wherein the vehicle traction apparatus further includes a control unit, wherein the control unit is adapted for controlling operation of the driving unit, each of the lifting driving mechanisms and each of the rotary driving mechanisms.

17. The radiation imaging check system according to claim 11, wherein the lifting driving mechanism includes a guiding shaft and a lifting oil cylinder, wherein:

the guiding shaft is disposed perpendicular to the ground, and is fixed on the body; and the lifting oil cylinder is disposed on the body and the wheel supporting assembly, for driving the wheel supporting assembly to move up or down along the guiding shaft.

18. The vehicle traction apparatus according to claim 11, wherein the vehicle traction apparatus comprises two balance tracks, each of which is disposed on an outer side of a corresponding one of the two tracks and parallels to the tracks, the two balance tracks are adapted for ensuring balance of forces applied on the wheel supporting assembly when it fixing the front wheels of the vehicle to be detected.

19. The vehicle traction apparatus according to claim 18, wherein the wheel supporting assembly comprises two front fork arms, two rear fork arms, and four rotary driving mechanisms, wherein:

the two front fork arms are respectively disposed on an inner side of the two tracks oppositely, and each of the two front fork arms is connected with a corresponding cantilever and is rotatable relative to corresponding cantilever in a horizontal plane;

the two rear fork arms are respectively disposed on an inner side of the two tracks oppositely, and respectively spaced apart from the two front fork arms in the direction parallel to the tracks, each of the rear fork arms is connected with a corresponding cantilever and is rotatable relative to the corresponding cantilever in a horizontal plane; and each of the four rotary driving mechanisms are adapted for driving a corresponding one of the two front fork arms and the two rear fork arms, to rotate to a position where the corresponding one of the two front fork arms and the two rear fork arms is parallel to the tracks or a position where the corresponding one of the two front fork arms and the two rear fork arms is perpendicular to the tracks.

20. The vehicle traction apparatus according to claim 19, wherein the lifting driving mechanism includes a guiding shaft and a lifting oil cylinder, wherein:

the guiding shaft is disposed perpendicular to the ground, and is fixed on the body; and the lifting oil cylinder is disposed on the body and the wheel supporting assembly, for driving the wheel supporting assembly to move up or down along the guiding shaft.

* * * * *